(12) United States Patent
Sakai et al.

(10) Patent No.: US 9,757,010 B2
(45) Date of Patent: Sep. 12, 2017

(54) IN VIVO INFORMATION ACQUIRING APPARATUS

(71) Applicant: OLYMPUS CORPORATION, Tokyo (JP)

(72) Inventors: Youhei Sakai, Ina (JP); Fukashi Yoshizawa, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 796 days.

(21) Appl. No.: 13/858,433

(22) Filed: Apr. 8, 2013

(65) Prior Publication Data

US 2013/0225923 A1 Aug. 29, 2013

Related U.S. Application Data

(63) Continuation of application No. PCT/JP2011/068282, filed on Aug. 10, 2011.

(30) Foreign Application Priority Data

Oct. 8, 2010 (JP) .................................. 2010-228974

(51) Int. Cl.
  *A61B 1/00* (2006.01)
  *A61B 1/04* (2006.01)
  (Continued)

(52) U.S. Cl.
  CPC ...... *A61B 1/00032* (2013.01); *A61B 1/00027* (2013.01); *A61B 1/041* (2013.01);
  (Continued)

(58) Field of Classification Search
  CPC ..... A61B 1/0638; A61B 1/041; A61B 5/0084; A61B 1/00009; A61B 1/00016;
  (Continued)

(56) References Cited

U.S. PATENT DOCUMENTS 8,674,825 B2 * 3/2014 Zdeblick .............. A61B 5/0031
    340/10.1
8,945,005 B2 * 2/2015 Hafezi ................... A61B 5/073
    340/572.1

(Continued)

FOREIGN PATENT DOCUMENTS

EP    1 961 366 A1    8/2008
JP    9-243469 A    9/1997
(Continued)

OTHER PUBLICATIONS

Extended Supplementary European Search Report dated Sep. 2, 2014 from European Application No. 11 83 0435.1.

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

A capsule endoscope includes: an in vivo information acquiring section that acquires information on an inside of a body of a subject; a battery that supplies power; a power source switch that turns on/off power supply from the battery to the in vivo information acquiring section; a detection section that includes at least two electrodes disposed on an outer face of a casing, and, upon detection of introduction to the inside of the body of the subject based on a change in electric resistance between the electrodes, outputs a detection signal; and a control section that controls the power source switch according to the detection signal.

9 Claims, 6 Drawing Sheets

(51) Int. Cl.
  *A61B 5/07* (2006.01)
  *A61B 5/00* (2006.01)
  *A61B 5/06* (2006.01)
(52) U.S. Cl.
  CPC .............. *A61B 5/073* (2013.01); *A61B 5/065* (2013.01); *A61B 5/4255* (2013.01); *A61B 2562/0204* (2013.01); *A61B 2562/0271* (2013.01)
(58) Field of Classification Search
  CPC . A61B 1/0684; A61B 5/14551; A61B 5/1459; A61B 5/1455; A61B 1/00032; A61B 2560/0209; A61B 2560/0219; A61B 5/0064
  USPC ................................ 600/117, 118, 178, 160
  See application file for complete search history.

(56) References Cited

U.S. PATENT DOCUMENTS

| | | | | |
|---|---|---|---|---|
| 2004/0253304 A1* | 12/2004 | Gross | ..................... | A61B 1/041 424/451 |
| 2004/0254419 A1* | 12/2004 | Wang | ..................... | A61K 45/06 600/8 |
| 2005/0065407 A1* | 3/2005 | Nakamura | ......... | A61B 1/00016 600/160 |
| 2006/0264734 A1* | 11/2006 | Kimoto | .............. | A61B 1/00016 600/407 |
| 2007/0129602 A1* | 6/2007 | Bettesh | .............. | A61B 1/00016 600/118 |
| 2007/0161851 A1* | 7/2007 | Takizawa | ........... | A61B 1/00156 600/102 |
| 2007/0171012 A1* | 7/2007 | Fujimori | ............ | A61B 1/00036 335/151 |
| 2008/0033242 A1* | 2/2008 | Tamura | .............. | A61B 1/00009 600/109 |
| 2008/0076965 A1* | 3/2008 | Yoshizawa | ......... | A61B 1/00016 600/103 |
| 2008/0108865 A1* | 5/2008 | Tamura | .................. | A61B 1/041 600/101 |
| 2008/0306360 A1* | 12/2008 | Robertson | .......... | A61B 1/00016 600/302 |
| 2009/0076352 A1* | 3/2009 | Fujita | ................. | A61B 1/00016 600/302 |
| 2009/0171146 A1* | 7/2009 | Fujita | ................. | A61B 1/00158 600/102 |
| 2009/0253954 A1* | 10/2009 | Katayama | .............. | A61B 1/045 600/103 |
| 2009/0264702 A1* | 10/2009 | Yoshizawa | ............. | A61B 5/073 600/117 |
| 2009/0292167 A1* | 11/2009 | Kimoto | .............. | A61B 1/00016 600/109 |
| 2010/0121150 A1 | 5/2010 | Fujimori et al. | | |
| 2010/0145149 A1* | 6/2010 | Yoshida | ................. | A61B 1/041 600/118 |
| 2010/0168517 A1* | 7/2010 | Shim | .................. | A61B 1/00016 600/117 |
| 2010/0268026 A1* | 10/2010 | Takizawa | ........... | A61B 1/00158 600/109 |
| 2010/0275934 A1* | 11/2010 | Keren | .................. | G01D 5/2066 128/899 |
| 2011/0224912 A1* | 9/2011 | Bhavaraju | ........... | G06F 19/3456 702/19 |
| 2012/0062371 A1* | 3/2012 | Radivojevic | ............ | G06F 3/016 340/407.1 |
| 2012/0101396 A1* | 4/2012 | Solosko | .............. | A61B 5/0006 600/509 |
| 2014/0139212 A1* | 5/2014 | Sakai | ................. | A61B 1/00036 324/244 |
| 2014/0139306 A1* | 5/2014 | Chiba | ................ | A61B 1/00158 335/306 |

FOREIGN PATENT DOCUMENTS

| | | |
|---|---|---|
| JP | 2001-224553 | 8/2001 |
| JP | 2005-080694 | 3/2005 |
| JP | 2007-160007 | 3/2005 |
| JP | 2005-110932 | 4/2005 |
| JP | 2006-109942 | 4/2006 |
| JP | 3151662 | 7/2009 |
| JP | 2010-094442 | 4/2010 |
| WO | WO 2007/069698 A1 | 6/2007 |
| WO | 2008/038848 A1 | 4/2008 |
| WO | 2010/047357 A1 | 4/2010 |

* cited by examiner

IN VIVO INFORMATION ACQUIRING APPARATUS

CROSS REFERENCE TO RELATED APPLICATION

This application is a continuation application of PCT/JP2011/068282 filed on Aug. 10, 2011 and claims benefit of Japanese Application No. 2010-228974 filed in Japan on Oct. 8, 2010, the entire contents of which are incorporated herein by this reference.

BACKGROUND OF THE INVENTION

1. Field of the Invention

The present invention relates to an in vivo information acquiring apparatus that is introduced to an inner portion of a subject and acquires information on an inside of a living body.

2. Description of the Related Art

In recent years, in the field of endoscopes, in vivo information acquiring apparatuses, which are swallow-type capsule endoscopes, have appeared. A capsule endoscope, which is swallowed from the mouth of a subject and thereby introduced to the inside of the body, has a function of moving inside body cavities, for example, organs such as the stomach and the small intestine according to peristaltic motion to sequentially pick up images until the capsule endoscope is naturally egested.

During the movement inside the body cavities, data of images picked up by the capsule endoscope inside the body is transmitted to the outside via wireless communication and accumulated in a memory provided inside an external receiver. After a patient swallows a capsule endoscope, the patient is free to do what he/she wants until the capsule endoscope is egested, carrying a receiver having the wireless communication function and the memory function with him/her.

A capsule endoscope obtains drive power from, e.g., a battery incorporated in its casing; however, it is impossible that a user performs an operation to turn on/off driving via, e.g., a switch disposed on an outer face of the casing because of its structure in which, e.g., an internal circuit is also sealed inside the casing. Therefore, capsule endoscopes including a switch inside their casings, the switch being turned on/off according to an external signal, have been proposed.

FIG. 1 illustrates a circuit diagram of a power source switch part of a capsule endoscope 110, which is disclosed in Japanese Patent Application Laid-Open Publication No. 2001-224553. In the capsule endoscope 110, power supply from a battery 119 to a main circuit is contactlessly switched on/off via a reed switch 112 whose contact point opens when the reed switch 112 is put in a magnetic field and a capacitor 112B. Also, for example, when the capsule endoscope 110 is being transported or is not used, the capsule endoscope 110 is stored in a packaging box or a storage case including a magnet, enabling a power source to be kept to be off

SUMMARY OF THE INVENTION

An in vivo information acquiring apparatus according to an embodiment of the present invention includes: an in vivo information acquiring section that acquires information on an inside of a body of a subject; a power source that supplies power; a power source switch that turns on/off power supply from the power source to the in vivo information acquiring section; a detection section that includes at least two electrodes disposed on an outer face of a casing, and, upon detection of introduction to the inside of the body of the subject based on a change in electric resistance between the electrodes, outputs a detection signal; and a control section that controls the power source switch according to the detection signal.

DETAILED DESCRIPTION OF THE PREFERRED EMBODIMENT

<First Embodiment>

A capsule endoscope (hereinafter also referred to as "capsule") 10, which is an in vivo information acquiring apparatus according to a first embodiment of the present invention, will be described below.

Figure 2:
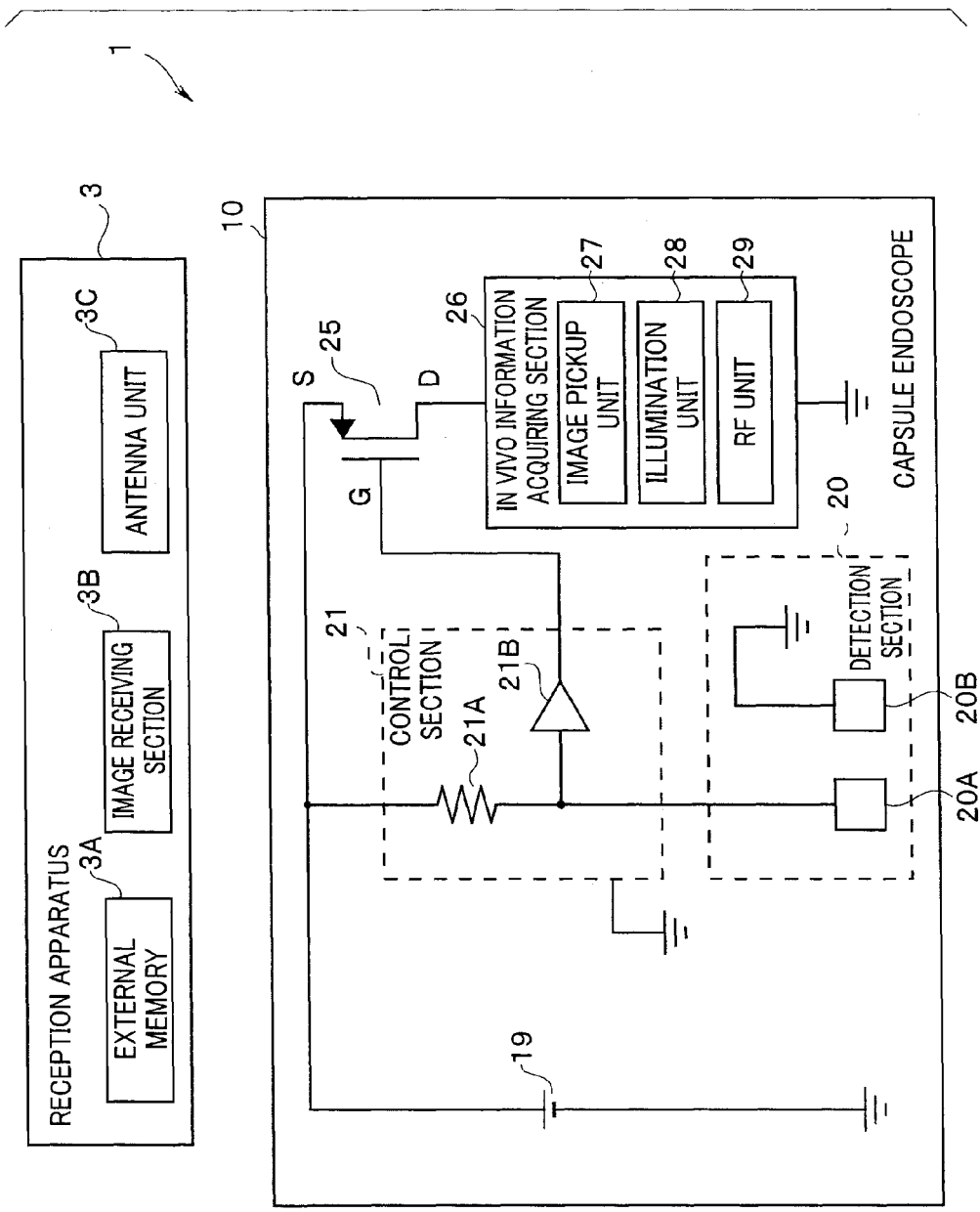
FIG. 2 is a configuration diagram for describing a configuration of a capsule endoscope according to a first embodiment.

As illustrated in FIG. 2, the capsule 10 provides an in vivo observation system 1 jointly with a reception apparatus 3 that receives an image signal from the capsule 10. The reception apparatus 3 includes an antenna unit 3C, an image receiving section 3B, and an external memory 3A that stores an image.

The capsule 10 includes a detection section 20, an in vivo information acquiring section 26, a battery 19, which is a power source, a control section 21, and a power source switch 25.

The in vivo information acquiring section 26, which acquires information on the inside of the body of a subject, includes an illumination unit 28, an image pickup unit 27 and an RF unit 29. The illumination unit 28 includes, for example, an LED 28A that illuminates a wall surface of an organ inside a body. The image pickup unit 27 includes a solid-state image pickup device such as a CCD 27A or a CMOS image sensor that picks up an image of the wall surface of the organ inside the body. The RF unit 29 includes a transmission circuit and a transmission antenna that wirelessly transmit video information obtained by the image pickup unit 27 to the outside of the body. The video information transmitted by the RF unit 29 is accumulated in an external memory 3A in the external reception apparatus 3.

Figure 1:
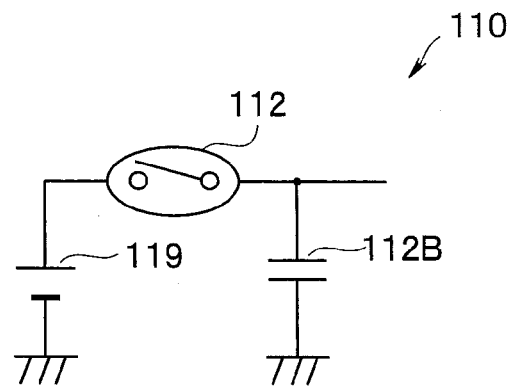
FIG. 1 is a circuit diagram of a power source switch part of a known capsule endoscope.
Figure 3:
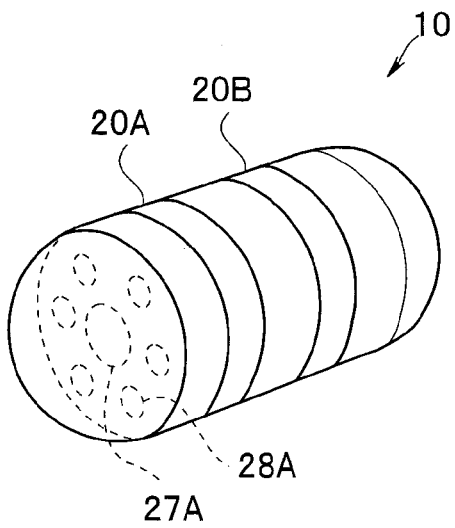
FIG. 3 is a diagram of an outer appearance of the capsule endoscope according to the first embodiment.

As illustrated in FIG. 3, the detection section 20 includes two electrodes 20A and 20B disposed on an outer face of a casing of the capsule 10. In other words, the capsule 10 has an elongated capsule shape, and an end portion at which the CCD 27A and the LED 28A are disposed has a dome shape formed by a transparent material, and a central cylindrical portion and an opposed dome-shaped end portion are each formed by a light-blocking material.

At the central cylindrical portion, the electrode 20A and the electrode 20B are disposed. When the capsule 10 is outside a body, the electrode 20A and the electrode 20B are isolated from each other, and when the capsule 10 is inside a body, the electrode 20A and the electrode 20B are substantially electrically connected by a body fluid, for example, a gastric fluid. In other words, the detection section 20 detects an impedance (electric resistance) between the electrode 20A and the electrode 20B to detect whether or not the capsule 10 is inside a living body (inside a body). Then, as will be described later, upon detection of introduction to the inside of the body of a subject, the detection section 20 outputs an L-level detection signal.

The power source switch 25, which performs on (supply)/off (interrupt) control of the power supply from the battery 19 to the in vivo information acquiring section 26 is, for example, a P-channel FET controlled by the control section 21. In other words, the power source switch 25 includes a source (S) connected to the battery 19, a gate (G) connected to an output of the control section 21 and a drain (D) connected to the in vivo information acquiring section 26. A part between the drain and the source of the power source switch 25 is opened or closed according to an input to the gate.

The control section 21 includes a buffer circuit 21B and a resistance 21A. An input terminal of the buffer circuit 21B is pulled up to a power source voltage by the resistance 21A and the input terminal of the buffer circuit 21B is connected to the electrode 20A of the detection section 20.

Next, an operation of the capsule 10 will be described.

When the capsule 10 is outside a body, an input to the buffer circuit 21B is pulled up by the resistance 21A, and a gate terminal of the power source switch 25 exhibits a high level (H level). Accordingly, the capsule 10 is in a quiescent state in which the power source switch 25 is in an open (off) state.

The capsule 10 is swallowed and thereby introduced to the inside of the body of a subject. Then, the electric resistance (impedance) between the electrode 20A and the electrode 20B of the detection section 20 is lowered by contact with an inner wall of the body or a liquid (e.g., saliva or gastric fluid) inside the body. When the impedance between the two electrodes is lowered, the detection section 20 outputs an L-level detection signal. Then, the input of the buffer circuit 21B exhibits a low level (L level), and an output of the buffer circuit 21B (gate voltage of the switch 25) exhibits an L level.

Then, the power source switch 25 enters a conducting (on) state, and the capsule 10 enters an activated state in which the power supply to the in vivo information acquiring section 26 is in an on state. As described above, in the capsule 10, the control section 21 controls the power source switch 25 according to the result of detection by the detection section 20.

The in vivo information acquiring section 26 in an activated state picks up an image at predetermined time intervals, and wirelessly transmits an image signal. The image signal transmitted by the in vivo information acquiring section 26 is received by the reception apparatus 3 and stored in the external memory 3A.

The impedance between the two electrodes (20A and 20B) when the capsule 10 is introduced to the inside of a body differs depending on, e.g., the site inside the body and the type of the body fluid which are in contact with the electrodes. However, the resistance 21A is made to have a resistance value sufficiently large relative to the impedance between the electrodes inside a body, enabling the input of the buffer circuit 21B to be an L level when the capsule 10 is introduced into a body.

The capsule 10 is in an off (stopped) state outside a body and in an on (activated) state inside a body under the control of the control section 21 that performs control according to a detection signal. Also, the power supply control for the capsule 10 is performed based only on a change in impedance between the two electrodes (20A and 20B). Accordingly, the power supply to the in vivo information acquiring section 26 is turned on from a point of time when the capsule 10 is introduced to the inside of a body, and the power supply is not turned off by, for example, application of a magnetic field from the outside.

In other words, although the capsule endoscope 10 has a simple configuration, the capsule endoscope 10 does not erroneously stop after introduction to the inside of a body.

Note that where it is necessary to check operation of the capsule 10 during a manufacturing process or before use, it is only necessary to short-circuit the two electrodes (20A and 20B). Also, a storage case used for, e.g., transport of the capsule 10 may include an insulating material to prevent the two electrodes 20A and 20B from being short-circuited inside the storage case.

Although the electrodes 20A and 20B illustrated in FIG. 2 here each have a shape surrounding the cylindrical portion, the electrodes may have any shape as long as the shape is a shape enabling detection of a change in impedance due to introduction to the inside of a body. Also, it is possible that the detection section 20 includes three or more electrodes and detects electrical connection between any two of the electrodes.

Figure 4A:
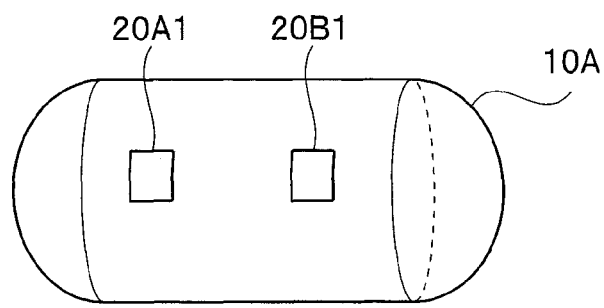
FIG. 4A is a diagram of an outer appearance of a capsule endoscope according to modification 1 of the first embodiment.
Figure 4B:
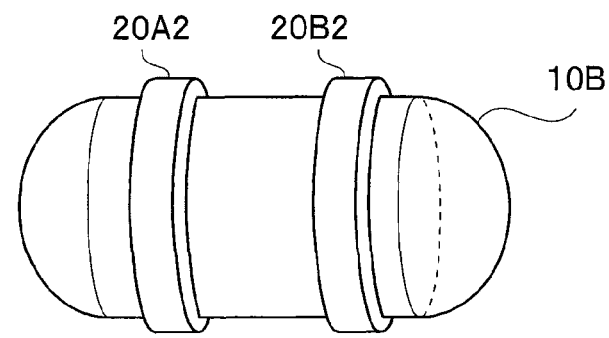
FIG. 4B is a diagram of an outer appearance of a capsule endoscope according to modification 2 of the first embodiment.
Figure 4C:
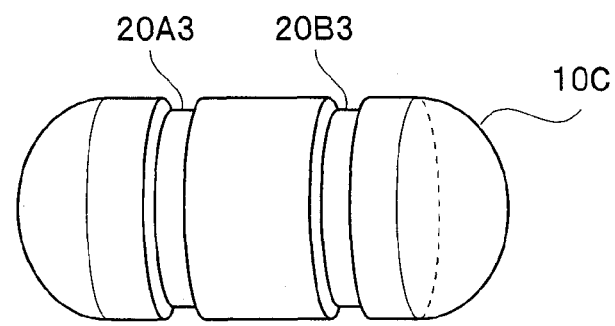
FIG. 4C is a diagram of an outer appearance of a capsule endoscope according to modification 3 of the first embodiment.
Figure 4D:
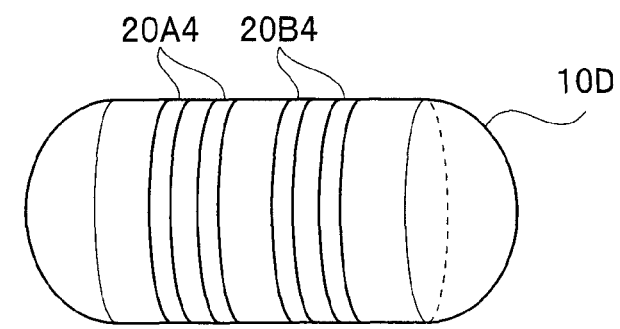
FIG. 4D is a diagram of an outer appearance of a capsule endoscope according to modification 4 of the first embodiment.

For example, electrodes 20A1 and 20B1 in a capsule endoscope 10A according to modification 1 of the present embodiment, which is illustrated in FIG. 4A, are pad electrodes exposed on an outer face of a casing. Electrodes 20A2 and 20B2 in a capsule endoscope 10B according to modification 2, which is illustrated in FIG. 4B, are each disposed in a ring shape along a casing and electrode portions each have a protrusion structure relative to a surface of the casing. Electrodes 20A3 and 20B3 in a capsule endoscope 10C according to modification 3, which is illustrated in FIG. 4C, are each disposed in a ring shape along a casing, and electrode portions each have a recess structure relative to a surface of the casing. Electrodes 20A4 and 20B4 in a capsule endoscope 10D according to modification 4, which is illustrated in FIG. 4D, are isolated from each other, and include four electrodes each disposed in a ring shape along a casing.

Note that a detection method in the detection section 20 may be one based on, e.g., a temperature sensor, a light sensor, a sound sensor, a pH sensor or an intra-body propagation signal sensor. For example, the sound sensor detects heart sounds peculiar to the inside of a body. Also, the intra-body propagation signal sensor detects a signal generated by a high-frequency signal generating apparatus outside a body and conveyed to the inside of the body via an external electrode disposed on a surface of the body of a subject.

<Second Embodiment>

Next, a capsule endoscope 10E according to a second embodiment of the present invention will be described. Since the capsule endoscope 10E according to the present embodiment is similar to the capsule endoscope 10 according to the first embodiment, only differences therebetween will be described.

Figure 5:
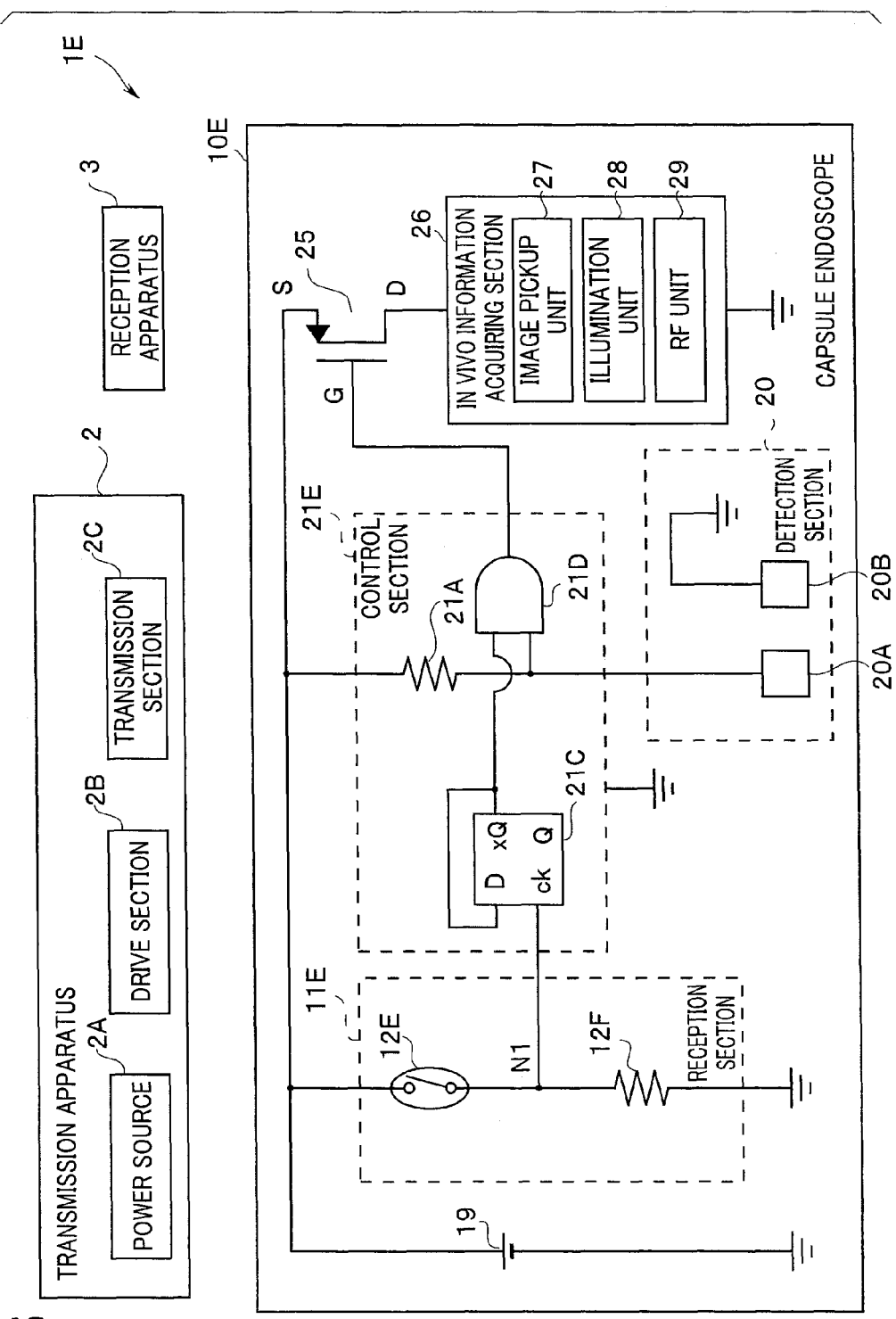
FIG. 5 is a configuration diagram for describing a configuration of a capsule endoscope according to a second embodiment.

As illustrated in FIG. 5, the capsule endoscope 10E provides an in vivo observation system 1E jointly with a transmission apparatus 2 that transmits a magnetic field signal from the outside of the capsule endoscope 10E and a reception apparatus 3 that receives an image signal from the capsule endoscope 10. The transmission apparatus 2 includes a power source 2A, a drive section 2B and a transmission section 2C, which is a magnetic field generating section.

The capsule endoscope 10E includes a signal receiving section (hereinafter also referred to as "reception section") 11E. The reception section 11E includes a reed switch 12E and a resistance 12F. In the reed switch 12E, respective one ends of two ferromagnetic leads are opposed to each other with a space therebetween and the reed switch 12E is enclosed in a glass tube. In the reed switch 12E, an N pole and an S pole are induced on the leads by an external magnetic field, and the leads are short-circuited by a magnetic attractive force and thereby the reed switch 12E enters a closed (on) state. Also, when the magnetic field is removed, the reed switch 12E is made to enter an open state (off) state by elasticity of the leads. The resistance 12F is a pull-down resistance for making an input voltage of a control section 21E exhibit an L level when the reed switch 12E enters an open state from a closed state.

The control section 21E includes a D flip-flop (FF) circuit 21C, which is a frequency dividing circuit, an AND circuit 21D and a resistance 21A. An xQ output of the flip-flop circuit 21C, which is a frequency dividing circuit, is connected to one input terminal of the AND circuit 21D.

The other input terminal of the AND circuit 21D is pulled up by the resistance 21A and is connected to an electrode 20A of a detection section 20.

An output of the AND circuit 21D, which is an output of the control section 21E, is connected to a gate of the power source switch 25. The output of the AND circuit 21D exhibits an L level except when the two input terminals both exhibit an H level.

Figure 6:
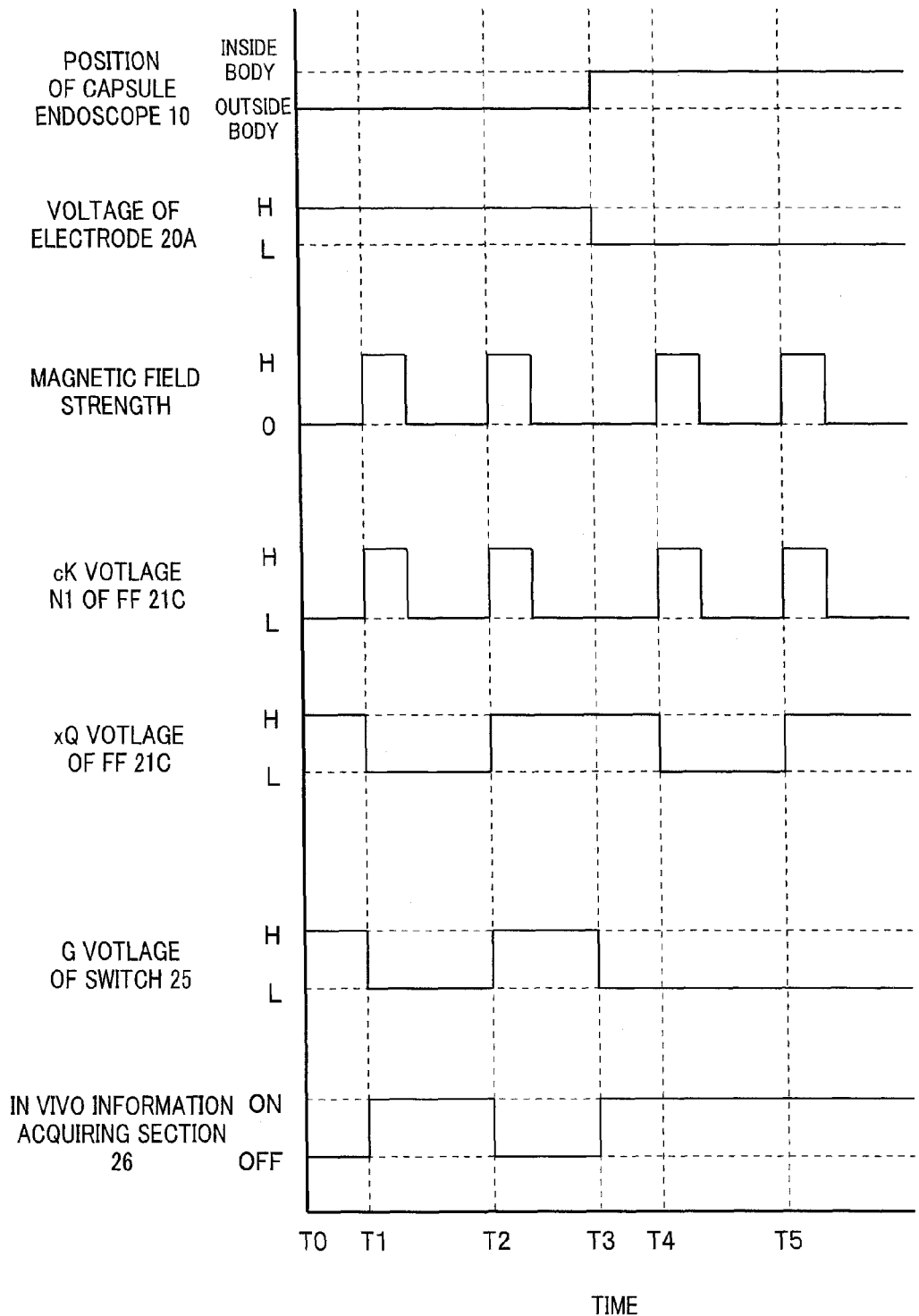
FIG. 6 is a time chart for describing an operation of the capsule endoscope according to the second embodiment.

An operation of the capsule endoscope 10E will be described below with reference to the time chart in FIG. 6. Note that, for sake of preventing a complicated description, the flip-flop circuit 21C operates according to raising edges.

In an initial state (T0 to T1), the capsule 10E is positioned outside a body, and an in vivo information acquiring section 26 is in an off state.

When a first magnetic field is applied at a time T1, the reed switch 12E is turned on, and only during a period in which the reed switch 12E is on, a node N1 exhibits an H level. In response to a voltage of the node N1, which is a voltage of a ck terminal that is an input, turning to an H level, the xQ output of the flip-flop circuit 21C is inverted from an H level to an L level and an L-level signal is inputted to the AND circuit 21D. The other input of the AND circuit 21D is pulled up by the resistance 21A, and since the electrode 20A is an open state, the output of the AND circuit 21D exhibits an L level, and the power source switch 25 is thereby turned on. Consequently, power supply to the in vivo information acquiring section 26 is turned on.

Upon application of a second magnetic field at a time T2, the reed switch 12E is turned on again, the xQ output of the flip-flop circuit 21C is inverted from an L level to an H level, and thus the power supply to the in vivo information acquiring section 26 is turned off.

In other words, when the capsule 10E is positioned outside a body, the power supply to the in vivo information acquiring section 26 is toggled from on to off or from off to on each time a magnetic field is applied.

Here, an operation when 10E is swallowed to the inside of a body will be described.

At a time T3, the capsule 10E is swallowed and inserted to the inside of a body. Then, an impedance between the electrode 20A and an electrode 20B is lowered by contact with an inner wall of the body or a liquid inside the body (e.g., saliva or gastric fluid). When the impedance between the two electrodes is lowered, the detection section 20 outputs an L-level detection signal. Then, one input of the AND circuit 21D exhibits an L level, and the output of the AND circuit 21D (gate voltage of the power source switch 25) exhibits an L level irrespective of the state of the other input. Consequently, the power source switch 25 is turned on and the power supply to the in vivo information acquiring section 26 is thereby turned on.

Although the impedance between the two electrodes differs depending on the site inside the body and/or the type of the body fluid, which are in contact with the electrodes, the resistance 21A is made to have a value sufficiently large relative to the impedance, enabling the input of the AND circuit 21D to exhibit an L level.

As a result of application of a third magnetic field at a time T4 and application of a fourth magnetic field at a time T5, the xQ output of the flip-flop circuit 21C transitions between an H level and an L level; however, the output of the AND circuit 21D does not change.

In other words, since the capsule endoscope 10E is introduced to the inside of the body, the power supply to the in vivo information acquiring section 26 is constantly in an on state, and thus, the capsule endoscope 10E does not erroneously stop due to magnetic field application from the outside.

The capsule endoscope 10E provides effects provided by the capsule 10 according to the first embodiment, and furthermore, can easily be turned on/off outside a body.

<Third Embodiment>

Next, a capsule endoscope 10F according to a third embodiment of the present invention will be described. Since the capsule endoscope 10F according to the present embodiment is similar to the capsule endoscope 10E according to the second embodiment, only differences therebetween will be described. In other words, a difference between the capsule endoscope 10F according to the present embodiment and the capsule 10E according to the second embodiment lies in that an alternating magnetic field is used as a control signal.

Figure 7:
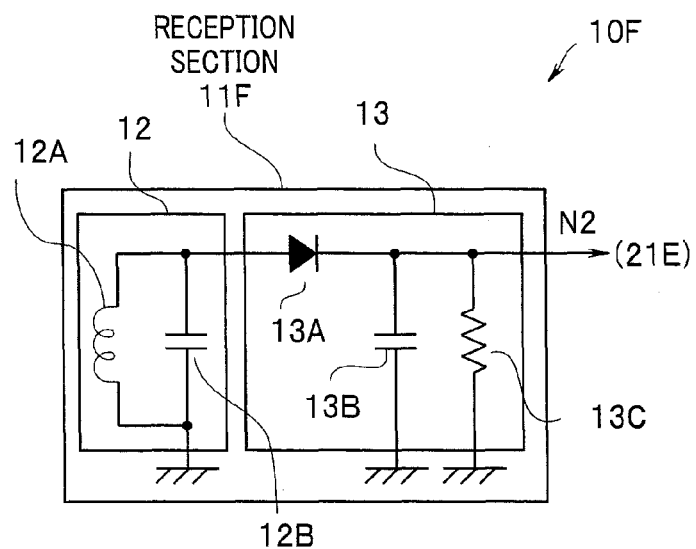
FIG. 7 is a configuration diagram for describing a configuration of a reception section in a capsule endoscope according to a third embodiment.

As illustrated in FIG. 7, a reception section 11F in the capsule endoscope 10F includes a reception sensor 12 and a reception circuit 13. The reception sensor 12 includes a magnetic field detection coil 12A that outputs an alternating current signal with a magnitude according to a strength of an alternating magnetic field and a resonance capacitor 12B. The reception circuit 13 includes a diode 13A and a capacitor 13B that rectify the alternating current signal outputted by the reception sensor 12 and a resistance 13C.

An alternating magnetic field signal from a transmission apparatus 2 is detected by the magnetic field detection coil 12A, and the detected alternating magnetic field signal is rectified and transmitted to a control section 21E, which is similar to the control section in the capsule 10E.

In the capsule 10F, the reception section 11F receives an alternating magnetic field from the outside by means of the reception sensor 12, and outputs a direct current signal via the reception circuit 13.

Figure 8:
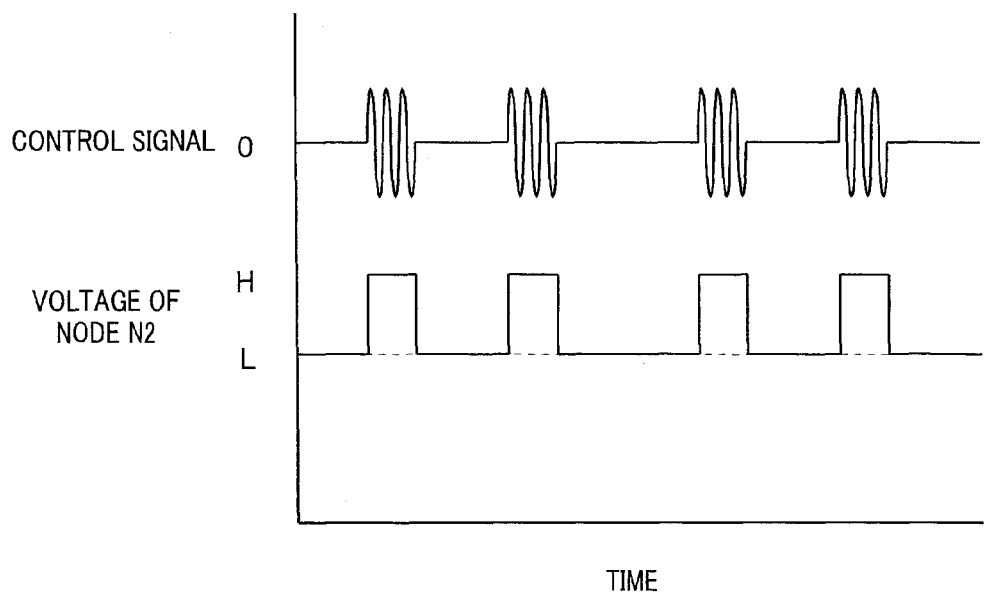
FIG. 8 is a time chart for describing an operation of the reception section in the capsule endoscope according to the third embodiment.

As illustrated in FIG. 8, only during periods in which an alternating magnetic field is applied to a node N2, an H-level control signal is outputted and conveyed to the control section 21E.

Since the node N2 corresponds to the node N1 in the first embodiment, the subsequent operation is similar to that of the capsule 10E according to the second embodiment.

In the capsule 10F according to the present embodiment, the reception section 11F receives an alternating magnetic field by means of the magnetic field detection coil 12A, and thus, the capsule 10F operates even with a relatively weak magnetic field and does not receive an alternating magnetic field with a different frequency. Thus, the capsule 10F provides effects provided by the capsule 10E and further provides an effect of prevention of erroneous activation due to vibration during, e.g. transport, or disturbing noise and a mechanical strength increasing effect.

Although the above description has been provided taking a capsule endoscope as an example of an in vivo information acquiring apparatus, an in vivo information acquiring system according to the present invention can be applied to various types of capsule in vivo information acquiring apparatuses such as capsule medical apparatuses for digestive organ fluid collection, capsule pH sensors and capsule temperature sensors.

The present invention is not limited to the above-described embodiments and modifications, and combinations of the embodiments and modifications, various variations, alterations and the like are possible without departing from the spirit of the present invention.

What is claimed is:

1. An in vivo information acquiring apparatus comprising:
   an in vivo information acquiring section that acquires information on an inside of a body of a subject;
   a power source that supplies power;
   a power source switch that turns on/off power supply from the power source to the in vivo information acquiring section;
   a detection section that includes at least two electrodes disposed on an outer face of a casing, and, upon detection of introduction to the inside of the body of the subject based on a change in electric resistance between the electrodes, outputs a detection signal;
   a control section that controls the power source switch according to the detection signal; and
   a signal receiving section that receives a control signal from an outside and outputs an internal signal,
   wherein the control section controls the power source switch according to the detection signal and the internal signal.

2. The in vivo information acquiring apparatus according to claim 1,
   wherein the casing comprises a cylindrical shape, and
   wherein the at least two electrodes are wound on the outer face of the cylindrical shape of the casing.

3. The in vivo information acquiring apparatus according to claim 2,
   wherein the at least two electrodes are each formed in a protrusion shape on the outer face of the cylindrical shape of the casing.

4. The in vivo information acquiring apparatus according to claim 2,
   wherein the at least two electrodes are each formed in a recess shape on the outer face of the cylindrical shape of the casing.

5. The in vivo information acquiring apparatus according to claim 1,
   wherein the control signal is an alternating magnetic field signal, and
   wherein the signal receiving section comprises:
      a magnetic field detection coil that receives the alternating magnetic field signal; and
      a reception circuit that rectifies the alternating magnetic field signal received by the magnetic field detection coil and outputs the internal signal.

6. The in vivo information acquiring apparatus according to claim 5, wherein upon receipt of the detection signal from the detection section that detects the introduction to the inside of the body of the subject, the control section controls the power source switch so as to turn on the power supply irrespective of the internal signal.

7. The in vivo information acquiring apparatus according to claim 6,
   wherein the in vivo information acquiring apparatus is a capsule endoscope, and
   wherein the in vivo information acquiring section comprises an image pickup section that picks up an image of the inside of the body of the subject.

8. The in vivo information acquiring apparatus according to claim 1,
   wherein upon receipt of the detection signal from the detection section that detects the introduction to the inside of the body of the subject, the control section controls the power source switch so as to turn on the power supply irrespective of the internal signal.

9. The in vivo information acquiring apparatus according to claim 8,
   wherein the in vivo information acquiring apparatus is a capsule endoscope, and
   wherein the in vivo information acquiring section comprises an image pickup section that picks up an image of the inside of the body of the subject.

* * * * *